United States Patent [19]

Lutz et al.

[11] 4,196,142

[45] Apr. 1, 1980

[54] 2-CHLORO-N-ISOPROPYL-3,5-DISUBSTITUTED OR 3,4,5-TRISUBSTITUTES LOWER ALKYL ACETANILIDES AS HERBICIDAL AGENTS

[75] Inventors: Albert W. Lutz, Princeton; Robert E. Diehl, Lawrenceville, both of N.J.

[73] Assignee: American Cyanamid Company, Stamford, Conn.

[21] Appl. No.: 875,463

[22] Filed: Feb. 6, 1978

Related U.S. Application Data

[63] Continuation-in-part of Ser. No. 774,357, Mar. 4, 1977, abandoned.

[51] Int. Cl.$^2$ .......................................... C07C 103/375
[52] U.S. Cl. .................................. 260/562 B; 71/118
[58] Field of Search ..................... 260/526 B, 562 B; 71/118

[56] References Cited

U.S. PATENT DOCUMENTS

| | | | |
|---|---|---|---|
| 3,960,948 | 6/1976 | Shackleton et al. | 260/562 B |
| 4,021,483 | 5/1977 | Lutz et al. | 260/562 B |
| 4,049,423 | 9/1977 | Baker et al. | 71/118 |
| 4,050,923 | 9/1977 | Baker et al. | 71/118 |

FOREIGN PATENT DOCUMENTS 2027822  12/1970  Fed. Rep. of Germany.

*Primary Examiner*—Arthur P. Demers
*Attorney, Agent, or Firm*—Harry H. Kline

[57] ABSTRACT

There are provided the compounds: 2-chloro-N-isopropyl-3',5'-dimethylacetanilide, 2-chloro-N-isopropyl-3',5'-diethylacetanilide, 2-chloro-N-isopropyl-3'-ethyl-5'-methylacetanilide, 2-chloro-N-isopropyl-3',4',5'-trimethylacetanilide, and 2-chloro-N-isopropyl-3',5'-dimethyl-4'-ethylacetanilide; a method for preparing the same; and a method for controlling undesirable plant species therewith.

2 Claims, No Drawings

2-CHLORO-N-ISOPROPYL-3,5-DISUBSTITUTED OR 3,4,5-TRISUBSTITUTES LOWER ALKYL ACETANILIDES AS HERBICIDAL AGENTS

This application is a continuation-in-part of our co-pending application, Ser. No. 774,357, filed on Mar. 4, 1977, now abandoned.

BACKGROUND OF THE INVENTION

Substituted chloroacylanilides are described in German Offenlegungsschrift No. 2,027,822, filed June 7, 1969. The applicants generically define a class of compounds which encompass the compounds of the subject invention, but do not identify them per se; nor do they recognize that 2-chloro-N-isopropyl-3',5'-dimethylacetanilide, 2-chloro-N-isopropyl-3',5'-diethylacetanilide and 2-chloro-N-isopropyl-3'-ethyl-5'-methylacetanilide, 2-chloro-N-isopropyl-3',5'-dimethyl-4'-ethylacetanilide, and 2-chloro-N-isopropyl-3',4',5'-trimethylacetanilide, are unique as possessing outstanding herbicidal properties. Further, French Pat. No. 1,337,529 discloses certain compounds which may be referred to as halogenated acetanilides. However, the patentees, like the German applicants, have likewise directed their attention toward compounds other than the compounds of the instant invention and have not recognized the superior herbicidal performance which is afforded by the 2-chloro-N-isopropyl-3',5'-disubstituted acetanilides of the present invention.

Insofar as the acetanilides of the present invention are concerned, the uniqueness of these compounds appears to be the result of either the 3',5'-dialkyl($C_1$–$C_2$) or 3',4',5'-trialkyl ($C_1$–$C_2$) substitution in the phenyl ring moiety; and such uniqueness is demonstrated not only by the herbicidal superiority of said compounds over their closest homologs, but also by their marked herbicidal superiority over isomeric relatives.

In addition to the French and German disclosures referred to above, it is noted that there are a number of issued United States patents disclosing a variety of haloacetanilides, including U.S. Pat. Nos. 2,863,752, issued Dec. 9, 1958; 3,268,584, issued Aug. 23, 1966; 3,475,157, issued Oct. 28, 1969 and 3,867,446, issued Feb. 18, 1975. As with the previously discussed disclosures, patentees therein do not disclose the above-mentioned 2-chloro-N-isopropyl-3',5'-dialkyl($C_1$–$C_2$) or -3',4',5'-trialkyl ($C_1$–$C_2$); acetanilides; nor do they suggest their unusual and unexpected character.

SUMMARY OF THE INVENTION

This invention relates to the compounds: 2-chloro-N-isopropyl-3',5'-dimethylacetanilide, 2-chloro-N-isopropyl-3',5'-diethylacetanilide and 2-chloro-N-isopropyl-3'-ethyl-5'methylacetanilide, and 2-chloro-N-isopropyl-3',4',5'-trimethyl- or 3',5'-dimethyl-4-ethylacetanilide, to a method for preparing the same, and to a method for the control of undesirable plant species therewith.

In accordance with the process of the present invention, 2-chloro-N-isopropyl-3',5'-dialkyl($C_1$–$C_2$) or 3',4',5'-trialkyl ($C_1$–$C_2$) acetanilides can be prepared for instance by the chloroacetylation of a N-isopropyl-3,5-dialkyl($C_1$–$C_2$) or 3,4,5-trialkyl($C_1$–$C_2$)aniline employing chloroacetic anhydride or chloroacetyl chloride. The reaction is conducted under anhydrous conditions, preferably in the presence of an inert organic solvent, such as benzene, chlorobenzene, toluene, xylene, diethyl ether, hexane or methylethylketone, at a temperature between about 50° C. and 150° C.

Preparation of the N-isopropyl-3,5-dialkyl($C_1$–$C_2$) or 3,4,5-trialkyl aniline can be achieved by the reductive alkylation of the appropriate 3,5-dialkyl($C_1$–$C_2$)aniline or 3,4,5-trialkyl($C_1$–$C_2$)aniline with acetone and 5A molecular sieves. The isolated intermediate is treated with sodium borohydride in a lower alcohol such as methanol, ethanol, n-propanol, isopropanol, n-butanol, or the like. It may also be prepared by the reductive alkylation of the appropriate 3,5-dialkyl($C_1$–$C_2$) or 3,4,5-trialkyl($C_1$–$C_2$)nitrobenzene with acetone using a noble metal catalyst, an acid promoter having pKa between 0.3 and 2.0, and preferably between 0.5 and 1.0, and hydrogen under superatmospheric pressure and at an elevated temperature. These reductive alkylations are graphically illustrated as follows:

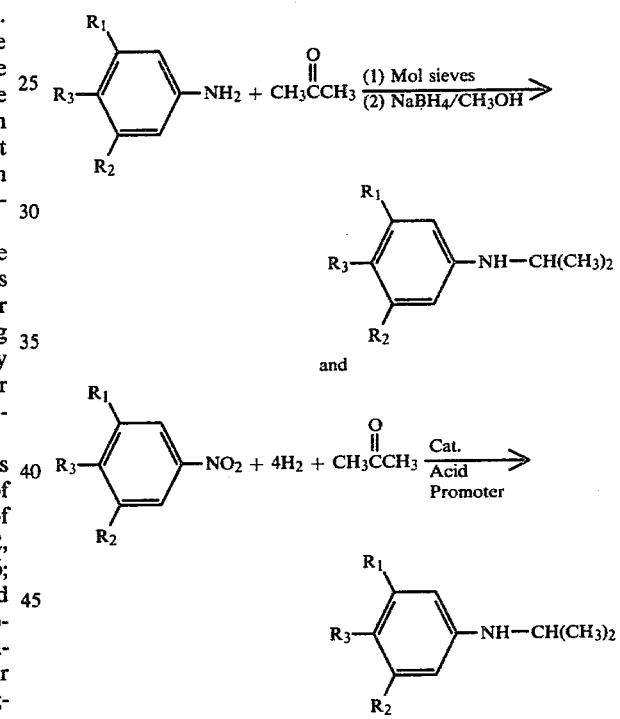

wherein $R_1$ and $R_2$ each individually represent methyl or ethyl and $R_3$ is hydrogen, methyl or ethyl and preferably where $R_3$ is ethyl, $R_1$ and $R_2$ are each methyl.

Chloroacetylation of the thus-prepared N-isopropyl-3,5-dialkyl or 3,4,5-trialkyl($C_1$–$C_2$)aniline yields the corresponding 2-chloro-N-isopropyl-3',5'-dialkyl($C_1$–$C_2$)acetanilide and this reaction is graphically illustrated as follows:

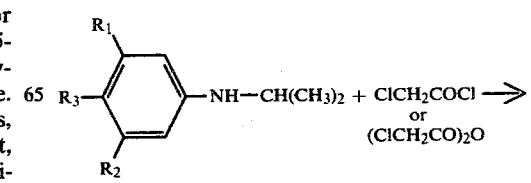

-continued

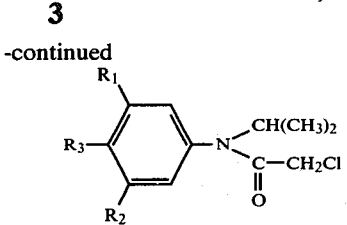

wherein $R_1$, $R_2$ and $R_3$ are each as above defined.

Among the noble metal catalysts that may be employed in the reductive alkylation of the 3,5-dialkylnitro-or 3,4,5-trialkylnitrobenzene are platinum and palladium, and these are preferably carried on a suitable support, such as carbon, silica or alumina.

In practice, the above-said catalyst is usually used in sufficient amount to provide at least 0.3 g of noble metal per mole of the 3,5-dialkylnitrobenzene or 3,4,5-trialkylnitrobenzene being alkylated.

The reductive alkylation is generally conducted in a pressure reactor under superatmospheric conditions and at an elevated temperature. Typically, a 3,5-dialkylnitro-or 3,4,5-trialkylnitrobenzene, acetone, noble metal catalyst and acid promoter are charged to a reactor. The reactor is then preferably deoxygenated by evacuation, followed by purging with nitrogen. The reactor is then pressurized to about 10 to 120 psig., and preferably 40 to 80 psig., with hydrogen gas and the reaction mixture is heated to between about 40° C. and 150° C., and preferably from 60° C. to 100° C. The reaction is generally completed in from 10 minutes to several hours, and when complete, the mixture is cooled and the pressure in the reactor reduced, as by venting.

In general, although the amount of acid promoter employed in the aforementioned reactions is preferably in the range of from 1 to 3 moles of acid per hundred moles of either 3,5-dialkylnitrobenzene or 3,4,5-trialkylnitrobenzene, as little as 0.1 mole of acid can be used per hundred moles of said dialkylnitrobenzene. Further, acetone and 3,5-dialkylnitrobenzene react on approximately an equimolar basis, but it has been found advantageous to employ an excess of acetone. It is generally preferable to employ a 1.1:1 to 2.2:1 ratio of acetone to the starting compound. It is also generally desirable to employ an aromatic sulfonic acid as the acid promoter. However, other acids having a pKa in the range of from 0.3 to 2.0 can also be utilized.

Additionally, it has been found that a mole ratio of metal catalyst to starting compound in the ratio of 0.05:1 to 0.15:1 is preferred. A large excess of hydrogen gas is, likewise, generally employed in the reaction.

Acids which can be used as promoters for the reductive alkylation include: $\beta$-naphthalene sulfonic acid, p-toluenesulfonic acid, ethylbenzenesulfonic acid, trichloroacetic acid, and the like.

Chloroacetylation of the N-isopropyl-3,5-dialkyl-or 3,4,5-trialkylaniline formed by either of the hereinabove-described processes, is achieved using a mole ratio of the chloroacetylating agent to N-isopropyl-3,5-dialkylaniline of from about 0.5:1 to 2.5:1, and, preferably about 1:1 to 2:1, respectively. The reaction is conducted under anhydrous conditions, preferably in the presence of an inert organic solvent, and preferably in the presence of an acid acceptor which will neutralize the acid formed by the reaction.

Typical acid acceptors which may be employed include: alkali metal and alkaline earth metal hydroxides, carbonates and bicarbonates.

The 2-chloro-N-isopropyl-3′,5′-dialkyl($C_1$–$C_2$) or 3′,3′,5′-trialkyl($C_1$–$C_2$)acetanilides of this invention are highly effective herbicidal agents. They can be used effectively for the control of undesirable broadleaf weeds and grasses by application thereof to the foliage of said undesirable broadleaf weeds and grasses, or by application thereof to soil containing seeds, rhizomes, rootbuds, or other propagating organs, of said undesirable plant species.

For postmergence control of undesirable plants, the compound is generally applied as a dilute aqueous spray in an amount sufficient to provide about 1.12 kg per hectare to 11.2 kg per hectare of the active ingredient, i.e. 2-chloro-N-isopropyl-3′,5′-dialkyl($C_1$–$C_2$) or 3′,4′,5′-trialkyl($C_1$–$C_2$)-acetanilide.

While the above-named compounds are effective for the postmergence control of undesirable plants, they are outstanding as selective preemergence herbicides. When used in this manner, it has been found that 2-chloro-N-isopropyl-3′,5′-dialkyl($C_1$–$C_2$) or 3′,4′,5′-trialkyl($C_1$–$C_2$)acetanilides will provide 85% or better control of undesirable grasses, such as crabgrass, barnyardgrass, Johnsongrass, Fall panicum, and the foxtails, at rates of application between 1/16 and 1/64 pound per acre (0.07 to 0.017 kg/hectare). It has been further found that at 1 pound per acre (1.12 kg/hectare), or from 16 to 64 times the effective rate for controlling undesirable grasses, this compound causes no injury to corn, cotton or sorghum crops.

For use as preemergence herbicides, 2-chloro-N-isopropyl-3′,5′-dialkyl($C_1$–$C_2$) or 3′,4′,5′-trialkyl($C_1$–$C_2$)-acetanilides may be applied at rates between 0.017 kg/hectare and 11.2 kg/hectare; however, they are preferably applied at rates between 0.07 kg/hectare and 4.48 kg/hectare, as dilute aqueous sprays. They may also be applied in the form of a finely divided solid, such as a dust or granular product, at the rates specified.

Aqueous sprays may be prepared by diluting an emulsifiable concentrate, a flowable liquid or wettable powder formulation containing the active ingredient, with water.

Typical emulsifiable concentrate, flowable liquid and wettable powder formulations are described below.

An emulsifiable concentrate formulation can be prepared by admixing 48%, by weight, of the 2-chloro-N-isopropyl-3′,5′-dialkyl($C_1$–$C_2$) or 3,4,5-trialkyl($C_1$–$C_2$)acetanilide with 28%, by weight, of monochlorobenzene, 18%, by weight, of a heavy aromatic solvent, 3%, by weight, of polyoxyethylene alkyl aryl ether/alkyl aryl sulfonate blend (surfactant), and 3%, by weight, of polyoxyethylene ether/polyoxyethylene glyceride alkyl aryl sulfonate blend (surfactant).

A flowable liquid can be prepared by grinding together 46.3%, by weight, of the 2-chloro-N-isopropyl-3′,5′-dialkyl ($C_1$–$C_2$) or 3′,4′,5′-trialkyl($C_1$–$C_2$)acetanilide, 3%, by weight, of sodium lignosulfonate, 1.0% bentonite or gelling clay and 49.7% water.

A wettable powder formulation can be prepared by grinding together 52.6%, by weight, of the above-identified acetanilide, 3.0%, by weight, of sodium lignosulfonate, 1.0%, by weight, of sodium N-methyl-N-oleoyl taurate and 43.4%, by weight of attaclay powder.

The present invention is further illustrated by the examples set forth below.

EXAMPLE 1

Preparation of N-Isopropyl-3,5-dimethylaniline.

3,5-Dimethylaniline (18.1 g, 0.15 mol) was dissolved in acetone (60 ml), the molecular sieves (30 g) added and then gently stirred at room temperature. After 24 hours, the sieves were removed by filtration and the excess acetone evaporated in vacuo. The resulting red oil was dissolved in methanol anol (75 ml), cooled to 10° C. and NaBH$_4$ added in small increments (30 minutes). It was then allowed to warm to 20° C., acidified cautiously with 10% HCl and then made basic with approximately 20% NaOH solution and extracted with ether. The ether solution was dried over anhydrous magnesium sulfate and the ether removed in vacuo giving 20.0 g of a red oil. This oil was vacuum distilled yielding 8.2 g (34%) of the desired product boiling at 72°–74°/0.5 mm.

Analysis calculated for NC$_{11}$H$_{17}$: C, 80.92; H, 10.49; N, 8.58. Found: C, 80.67; H, 11.23; N, 7.72.

Following the above procedure, but substituting 3,5-diethylaniline, 3-ethyl-5-methylaniline, 3,4,5-trimethylaniline or 3,5-dimethyl-4-ethylaniline for 3,5-dimethylaniline, there is obtained the corresponding N-isopropyl-3,5-diethyl-(or 3-ethyl-5-methyl)aniline, N-isopropyl-3,4,5-trimethylaniline or N-isopropyl-3,5-dimethyl-4-ethylaniline, respectively.

EXAMPLE 2

Preparation of
2-Chloro-N-isopropyl-3',5'-dimethylacetanilide.

N-isopropyl-3,5-dimethylaniline (5 g, 0.03 mol) and chloroacetic anhydride (5.3 g, 0.031 mol) were dissolved in molecular sieve dried benzene (35 ml) and heated to reflux for 4 hours. The reaction mixture was cooled and the benzene solution washed with water (2×40 ml), dilute hydrochloric acid (2×30 ml) and again with water (3×40 ml). After drying over anhydrous magnesium sulfate, benzene was removed in vacuo yielding 7.4 g (100%) of a red oil. After treatment with pentane, 5.1 g (69%) of a white solid was obtained; melting point 98°–100° C.

Analysis calculated for NOClC$_{13}$H$_{18}$: C, 65.13; H, 7.56; N, 5.84. Found: C, 65.24; H, 7.66; N, 5.89.

Following the above procedure, but substituting N-isopropyl-3,5-diethylaniline or N-isopropyl-3-ethyl-5-methylaniline, N-isopropyl-3',4',5'-trimethylaniline and N-isopropyl-3,5-dimethyl-4-ethylaniline for N-isopropyl-3,5-dimethylaniline, yields the corresponding 2-chloro-N-isopropyl-3',5'-diethyl (or 3'-ethyl-5'-methyl)acetanilide, 2-chloro-N-isopropyl-3',4',5'-trimethylacetanilide or 2-chloro-N-isopropyl-3',5'-dimethyl-4'-ethylacetanilide.

EXAMPLE 3

Selected Preemergence Herbicidal Activity.

The selective preemergence herbicidal activity of test compounds is evaluated by the following procedure. In these tests, seeds of a variety of broadleaf weeds, grass and crop plants are separately mixed with potting soil, Princeton soil or Wisconsin soil, and the mixtures placed on three to five cms. of the corresponding soil in separate cups. After planting, the cups are sprayed with the selected 50/50 aqueous acetone solution containing the test compound in sufficient quantity to provide the desired equivalent of from 0.017 kg/hectare to 1.12 kg/hectare per cup. The treated cups are then placed on greenhouse benches and cared for in the usual manner, in accordance with greenhouse procedures. Three weeks after treatment, the tests are terminated and each cup is examined and rated according to the defined Herbitoxicity Index given in each of the tables below.

| HERBITOXICITY INDEX | | |
|---|---|---|
| Rating | Meaning | % Different from the Control |
| 9 | Complete kill | 100 |
| 8 | Approaching complete kill | 91–99 |
| 7 | Good herbicidal effect | 76–90 |
| 6 | Herbicidal effect | 61–75 |
| 5 | Definite injury | 41–60 |
| 4 | *(See below) | — |
| 3 | Moderate effect | 26–40 |
| 2 | Slight effect | 11–25 |
| 1 | Possible effect | 1–10 |
| 0 | No effect | 0 |

*Test species are observed for plant growth regulant effects of the chemicals during all herbicide evaluations. If such effects occur, a rating of 4 is entered for the species affected.

Abbreviations for the plant species employed in the herbicidal evaluations hereinafter reported.
PN—Purple Nutsedge (*Cyperus rotundus* L.)
LA—Lambsquarters (*Chenopodium album*)
PI—Pigweed (*Amaranthus retroflexus*)
FP—Fall Panicum (*Panicum dichotomiflorum*)
DB—Downy Brome (*Bromus tectorum* L.)
BA—Barnyardgrass (*Echinochloa crusgalli*)
CR—Crabgrass (*Digitaria sanguinalis*)
GF—Green Foxtail (*Setaria viridis*)
YF—Yellow Foxtail (*Setaria glauca* L.)
GIF—Giant Foxtail (*Setaria faberri* Herrm.)
JG—Johnsongrass (*Sorghum halepense* L.)
PR—Perennial Ryegrass (*Lolium multiforum* Lam.)
CO—Cotton (*Gossypium hirsutum*)
CN—Corn (*Zea mays*)
SY—Soybean (*Glycine max*)

Data obtained are reported in Table I below where it can be seen that 2-chloro-N-isopropyl-3',5'-dimethylacetanilide provides 85% or more control of several undesirable grasses when applied at a rate of from 0.07 kg/hectare to 0.017 kg/hectare. If can also be seen that at 1.12 kg/hectare, corn and cotton showed no sign of injury.

TABLE I

| | Selective Preemergence Herbicidal Activity in Princeton Soil | | | | | | | | | | | | | | |
|---|---|---|---|---|---|---|---|---|---|---|---|---|---|---|---|
| | Rate | Plant Species | | | | | | | | | | | | | |
| Compound | kg/Hectare | PN | LA | PI | FP | DB | BA | CR | GF | YF | GIF | JG | PR | CO | CN | SY |

TABLE I-continued

| Compound | Rate kg/Hectare | | | | | | | | | | | | | | | |
|---|---|---|---|---|---|---|---|---|---|---|---|---|---|---|---|---|
| 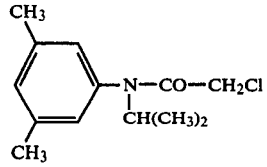<br>Compound of the Invention | 1.12<br>0.56<br>0.28<br>0.14<br>0.07<br>0.035<br>0.017 | 6<br>0<br>0<br>0<br>0<br>0<br>0 | 7<br>5<br>2<br>2<br>0<br>0<br>0 | 8<br>8<br>7<br>5<br>3<br>0<br>0 | 9<br>9<br>8<br>9<br>7<br>3<br>3 | 8<br>9<br>3<br>3<br>0<br>0<br>0 | 9<br>9<br>9<br>9<br>9<br>7<br>5 | 9<br>9<br>9<br>9<br>8<br>9<br>8 | 9<br>9<br>9<br>8<br>8<br>7<br>5 | 9<br>9<br>9<br>8<br>6<br>3<br>0 | 8<br>9<br>8<br>8<br>7<br>2<br>2 | 9<br>9<br>7<br>6<br>5<br>2<br>1 | 7<br>6<br>3<br>0<br>0<br>0<br>0 | 0<br>0<br>0<br>0<br>0<br>0<br>0 | 0<br>0IN-<br>0<br>0<br>0<br>0<br>0 | 5<br>5<br>3<br>3<br>3<br>2<br>2 |
| 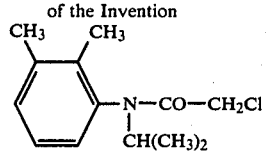<br>Positional Isomer | 1.12<br>0.56<br>0.28<br>0.14<br>0.07<br>0.035<br>0.017 | 0<br>0<br>0<br>0<br>0<br>0<br>0 | 3<br>0<br>0<br>0<br>0<br>0<br>0 | 6<br>3<br>2<br>0<br>0<br>0<br>0 | 9<br>8<br>8<br>7<br>5<br>0<br>0 | 8<br>6<br>0<br>0<br>0<br>0<br>0 | 9<br>9<br>8<br>9<br>6<br>3<br>0 | 9<br>9<br>8<br>8<br>5<br>3<br>0 | 9<br>9<br>8<br>8<br>7<br>6<br>3 | 8<br>8<br>7<br>6<br>6<br>3<br>0 | 8<br>8<br>7<br>7<br>3<br>3<br>2 | 7<br>7<br>5<br>2<br>0<br>0<br>0 | 8<br>6<br>0<br>0<br>0<br>0<br>0 | 0<br>0<br>0<br>0<br>0<br>0<br>0 | 0<br>0<br>0<br>0<br>0<br>0<br>0 | 3<br>5<br>3<br>2<br>6<br>3<br>1 |

Selective Preemergence Herbicidal Activity in Wisconsin Soil

| Compound | Rate kg/Hectare | PN | LA | PI | FP | DB | BA | CR | GF | YF | GIF | JG | PR | CO | CN | SY |
|---|---|---|---|---|---|---|---|---|---|---|---|---|---|---|---|---|
| 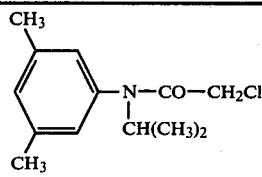<br>Compound of the Invention | 1.12<br>0.56<br>0.28<br>0.14<br>0.07<br>0.035<br>0.017 | 2<br>0<br>0<br>0<br>0<br>0<br>0 | —<br>—<br>—<br>—<br>—<br>—<br>— | 9<br>9<br>9<br>8<br>9<br>9<br>0 | 9<br>9<br>8<br>8<br>8<br>0<br>0 | 8<br>8<br>2<br>0<br>0<br>0<br>0 | 9<br>9<br>8<br>7<br>7<br>3<br>0 | 9<br>9<br>9<br>8<br>9<br>7<br>2 | 9<br>9<br>9<br>9<br>6<br>3<br>0 | 9<br>9<br>8<br>3<br>3<br>0<br>0 | 9<br>7<br>8<br>6<br>5<br>3<br>0 | 9<br>7<br>5<br>0<br>0<br>0<br>0 | 7<br>6<br>3<br>0<br>0<br>0<br>0 | 0<br>0<br>0<br>0<br>0<br>0<br>0 | 0<br>0<br>0<br>0<br>0<br>0<br>0 | 9<br>0<br>0<br>0<br>0<br>0<br>0 |
| 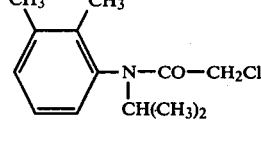<br>Positional Isomer | 1.12<br>0.56<br>0.28<br>0.14<br>0.07<br>0.035<br>0.017 | 0<br>0<br>0<br>0<br>0<br>0<br>0 | —<br>—<br>—<br>—<br>—<br>—<br>— | 9<br>9<br>8<br>9<br>0<br>0<br>0 | 8<br>8<br>8<br>5<br>5<br>0<br>0 | 0<br>0<br>0<br>0<br>0<br>0<br>0 | 9<br>9<br>7<br>7<br>3<br>0<br>0 | 9<br>9<br>9<br>6<br>3<br>0<br>0 | 9<br>9<br>8<br>7<br>6<br>3<br>0 | 9<br>9<br>8<br>6<br>5<br>0<br>0 | 8<br>8<br>7<br>6<br>3<br>0<br>0 | 3<br>2<br>0<br>0<br>0<br>0<br>0 | 7<br>5<br>0<br>0<br>0<br>0<br>0 | 0<br>0<br>0<br>0<br>0<br>0<br>0 | 0<br>0<br>0<br>0<br>0<br>0<br>0 | 0<br>0<br>0<br>0<br>0<br>0<br>0 |

Selective Preemergence Herbicidal Activity in Potting Soil

| Compound | Rate kg/Hectare | PN | LA | PI | FP | DB | BA | CR | GF | YF | GIF | JG | PR | CO | CN | SY |
|---|---|---|---|---|---|---|---|---|---|---|---|---|---|---|---|---|
| 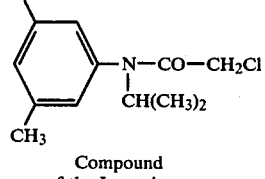<br>Compound of the Invention | 1.12<br>0.56<br>0.28<br>0.14<br>0.07<br>0.035<br>0.017 | 0<br>0<br>0<br>0<br>0<br>0<br>0 | 7<br>2<br>0<br>0<br>0<br>0<br>0 | 9<br>9<br>0<br>0<br>0<br>0<br>0 | 9<br>9<br>9<br>9<br>8<br>5<br>0 | 0<br>0<br>0<br>0<br>0<br>0<br>0 | 9<br>9<br>9<br>9<br>7<br>7<br>0 | 9<br>9<br>9<br>9<br>8<br>5<br>5 | 9<br>9<br>9<br>9<br>8<br>7<br>0 | 9<br>9<br>8<br>7<br>5<br>2<br>0 | 9<br>9<br>8<br>7<br>5<br>6<br>1 | 9<br>7<br>3<br>0<br>0<br>0<br>0 | 5<br>3<br>0<br>0<br>0<br>0<br>0 | 0<br>0<br>0<br>0<br>0<br>0<br>0 | 0<br>0<br>0<br>0<br>0<br>0<br>0 | 6<br>0<br>0<br>0<br>0<br>0<br>0 |
| 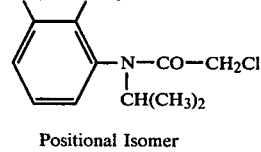<br>Positional Isomer | 1.12<br>0.56<br>0.28<br>0.14<br>0.07<br>0.035<br>0.017 | 0<br>0<br>0<br>0<br>0<br>0<br>0 | 0<br>0<br>0<br>0<br>0<br>0<br>0 | 0<br>0<br>0<br>0<br>0<br>0<br>0 | 8<br>8<br>7<br>2<br>0<br>0<br>0 | 0<br>0<br>0<br>0<br>0<br>0<br>0 | 9<br>9<br>8<br>5<br>0<br>0<br>0 | 8<br>8<br>6<br>2<br>0<br>0<br>0 | 9<br>9<br>7<br>7<br>5<br>1<br>0 | 9<br>8<br>6<br>5<br>1<br>0<br>0 | 8<br>8<br>7<br>7<br>5<br>0<br>0 | 0<br>0<br>0<br>0<br>0<br>0<br>0 | 5<br>2<br>0<br>0*-<br>0<br>0<br>0<br>0 | 0<br>0<br>0<br>0<br>0<br>0<br>0 | 0<br>0<br>0<br>0<br>0<br>0<br>0 | 0<br>0<br>0<br>0<br>0<br>0<br>0 |

EXAMPLE 4

The preemergence herbicidal activity of test compounds is evaluated by the following procedure, wherein the seeds of a variety of monocotyledonous and dicotyledonous plants are separately mixed with potting soil and planted on top of approximately 3 to 5 cm of soil in separate cups. After planting, the cups are sprayed with the selected 50/50 aqueous acetone solution containing test compound in sufficient quantity to provide the equivalent of 0.14 to 2.24 kg/hectare of test compound per cup. The treated cups are then placed on greenhouse benches, watered and cared for in accordance with conventional greenhouse procedures. Three weeks after treatment, the tests are terminated and the cups examined and rated using the rating system described in Example 3. Data obtained are reported in Table II below.

Abbreviations of plant species employed in these evaluations are:

SE—Sesbania (*Sesbania punicea* Cav.)

MU—Mustard (*Brassica kaber*)
PI—Pigweed (*Amaranthus retroflexus*)

SY—Soybean (*Glycine max*) and RI—Rice (*Oryza sativa*)

TABLE II

Preemergence Herbicidal Evaluation of Test Compounds

| Compound | Rate kg/Hectare | SE | MU | PI | RW | MG | TW | VL | BA | CR | GF | CN | CO | SY | RI |
|---|---|---|---|---|---|---|---|---|---|---|---|---|---|---|---|
| 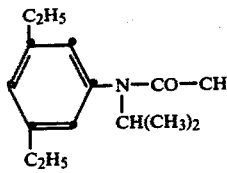 | 1.12 | 0 | 0 | 0 | 0 | 0 | 0 | 0 | 9 | 9 | 8 | 0 | 0 | 0 | 0 |
|  | 0.56 | 0 | 0 | 0 | 0 | 0 | 0 | 0 | 9 | 8 | 8 | 0 | 0 | 0 | 0 |
|  | 0.28 | 0 | 0 | 0 | 0 | 0 | 0 | 0 | 9 | 8 | 7 | 0 | 0 | 0 | 0 |
|  | 0.14 | 0 | 0 | 0 | 0 | 0 | 0 | 0 | 7 | 6 | 3 | 0 | 0 | 0 | 0 |
|  | 0.07 | 0 | 0 | 0 | 0 | 0 | 0 | 0 | 8 | 3 | 1 | 0 | 0 | 0 | 0 |
| Compound of the Invention 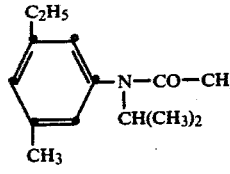 | 1.12 | 9 | 0 | 7 | 0 | 0 | 7 | 1 | 9 | 9 | 9 | 0 | 0 | 0 | 0 |
|  | 0.56 | 0 | 0 | 0 | 0 | 0 | 0 | 0 | 9 | 9 | 9 | 0 | 0 | 0 | 0 |
|  | 0.28 | 0 | 0 | 0 | 0 | 0 | 0 | 0 | 9 | 8 | 8 | 0 | 0 | 0 | 0 |
|  | 0.14 | 0 | 0 | 0 | 0 | 0 | 0 | 0 | 8 | 7 | 6 | 0 | 0 | 0 | 0 |
|  | 0.07 | 0 | 0 | 0 | 0 | 0 | 0 | 0 | 7 | 5 | 3 | 0 | 0 | 0 | 0 |
| Compound of the Invention 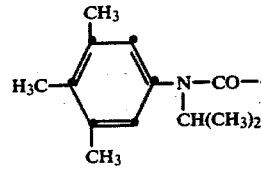 | 1.12 | 0 | 0 | 0 | 0 | 0 | 0 | 0 | 9 | 9 | 8 | 0 | 0 | 0 | 0 |
|  | 0.56 | 0 | 0 | 0 | 0 | 0 | 0 | 0 | 9 | 8 | 8 | 0 | 0 | 0 | 0 |
|  | 0.28 | 0 | 0 | 0 | 0 | 0 | 0 | 0 | 8 | 8 | 9 | 0 | 0 | 0 | 0 |
|  | 0.14 | 0 | 0 | 0 | 0 | 0 | 0 | 0 | 9 | 7 | 3 | 0 | 0 | 0 | 0 |
|  | 0.07 | 0 | 0 | 0 | 0 | 0 | 0 | 0 | 3 | 3 | 1 | 0 | 0 | 0 | 0 |
| Compound of the Invention 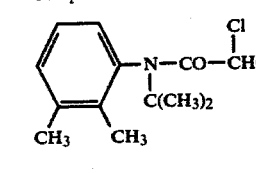 | 2.24 | 0 | 0 | 0 | 0 | 0 | 0 | 0 | 0 | 0 | 0 | 0 | 0 | 0 | 0 |
|  | 1.12 | 0 | 0 | 0 | 0 | 0 | 0 | 0 | 0 | 0 | 0 | 0 | 0 | 0 | 0 |
|  | 0.56 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 |
|  | 0.14 | 0 | 0 | 0 | 0 | 0 | 0 | 0 | 0 | 0 | 0 | 0 | 0 | 0 | 0 |
| Analog 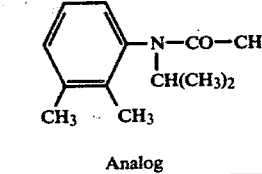 | 2.24 | 0 | 2 | 0 | — | 0 | 0 | 0 | 9 | 0 | 8 | 0 | 0 | 0 | 0 |
|  | 1.12 | 0 | 0 | 0 | 0 | 0 | 0 | 0 | 8 | 0 | 7 | 0 | 0 | 0 | 0 |
|  | 0.56 | 0 | 0 | 0 | — | 0 | 0 | 0 | 2 | 0 | 2 | 0 | 0 | 0 | 0 |
|  | 0.28 | 0 | 0 | 0 | — | 0 | 0 | 0 | 0 | 0 | 0 | 0 | 0 | 0 | 0 |
|  | 0.14 | 0 | 0 | 0 | 0 | 0 | 0 | 0 | 0 | 0 | 0 | 0 | 0 | 0 | 0 |

Analog

RW—Ragweed (*Ambrosia artemisiifolia*)
MG—Morningglory (*Ipomea purpurea*)
TW—Teaweed (*Sida spinosa*)
VL—Velvetleaf (*Abutilon theopharasti*)
BA—Barnyardgrass (*Echinochloa crusgalli*)
CR—Crabgrass (*Digitaria sanguinalis*)
GF—Green Foxtail (*Setaria viridis*)
CN—Corn (*Zea mays*)
CO—Cotton (*Gossypium hirsutum*)

EXAMPLE 5

Following the procedure of Example 4, but using Yellow Foxtail, Giant Foxtail, Fall Panicum, Downy Brome, Barnyardgrass, Crabgrass, Green Foxtail, Perennial Ryegrass, Corn, Cotton, Soybeans and Sorghum as the plant species, test compounds were evaluated as preemergence herbicidal agents. Compounds were applied at rates of from 0.035 kg per hectare to 1.12 kg/hectare. Data obtained are provided in Table III.

TABLE III

Preemergence Herbicidal Evaluations of Test Compounds

| Compound | Rate kg/hectare | BA | CR | GF | PR | YF | GIF | FP | DB | CN | CO | SY | SO |
|---|---|---|---|---|---|---|---|---|---|---|---|---|---|
| CH$_3$-C$_6$H$_3$(CH$_3$)-N(CH(CH$_3$)$_2$)-CO-CH$_2$Cl | 1.12 | 9 | 9 | 9 | 9 | 9 | 9 | 9 | 9 | 0 | 3 | 0 | — |
|  | 0.56 | 9 | 9 | 9 | 8 | 8 | 9 | 9 | 3 | 0 | 2 | 0 | 0 |
|  | 0.28 | 9 | 9 | 9 | 7 | 7 | 9 | 9 | 3 | 0 | 0 | 0 | 0 |
|  | 0.14 | 9 | 9 | 9 | 5 | 8 | 7 | 7 | 0 | 0 | — | 0 | 0 |
|  | 0.07 | 9 | 9 | 8 | 2 | 6 | 7 | 6 | 0 | 0 | 0 | 0 | 0 |
|  | 0.035 | 6 | 6 | 6 | 0 | 3 | 5 | 5 | 0 | 0 | 0 | 0 | 0 |
| Compound of the Invention 2,6-(CH$_3$)$_2$-C$_6$H$_3$-N(CH(CH$_3$)$_2$)-CO-CH$_2$Cl | 1.12 | 8 | 9 | 8 | 8 | 7 | 9 | 8 | 7 | 0 | 0 | 0 | 7 |
|  | 0.56 | 8 | 9 | 8 | 8 | 7 | 8 | 6 | 3 | 0 | 0 | 0 | 5 |
|  | 0.28 | 8 | 8 | 8 | 6 | 7 | 8 | 5 | 0 | 0 | — | 0 | 0 |
|  | 0.14 | 7 | 8 | 7 | 3 | 5 | 7 | 2 | 0 | 0 | 0 | 0 | 0 |
|  | 0.07 | 6 | 6 | 6 | 0 | 5 | 7 | 0 | 0 | 0 | 0 | 0 | 0 |
|  | 0.035 | 0 | 2 | 3 | 0 | 0 | 0 | 0 | 0 | 0 | 0 | 0 | 0 |
| Positional Isomer 3,4-(CH$_3$)$_2$-C$_6$H$_3$-N(CH(CH$_3$)$_2$)-CO-CH$_2$Cl | 1.12 | 9 | 9 | 9 | 6 | 7 | 9 | 8 | 7 | 0 | 0 | 0 | 0 |
|  | 0.56 | 9 | 9 | 8 | 5 | 7 | 8 | 8 | 0 | 0 | 0 | 0 | — |
|  | 0.28 | 9 | 8 | 8 | 3 | 5 | 5 | 6 | 0 | 0 | 0 | 0 | 0 |
|  | 0.14 | 9 | 7 | 6 | 0 | 3 | 6 | 3 | 0 | 0 | 0 | 0 | 0 |
|  | 0.07 | 9 | 6 | 6 | 0 | 2 | 2 | 3 | 0 | 0 | 0 | 0 | 0 |
|  | 0.035 | 3 | 2 | 3 | 0 | 0 | 0 | 0 | 0 | 0 | 0 | 0 | 0 |

Positional Isomer

SO - Sorghum (*Sorghum vulgare*)

EXAMPLE 6

The selective preemergence herbicidal activity of the compounds of the present invention is further evaluated in the following side-by-side tests using potting soil and the plant species and test procedure of Example 4 above. Data obtained are reported in Table IV below.

TABLE IV

Selective Preemergence Herbicidal Activity of Test Compounds

| Compound | Rate kg/Hectare | PN | LA | PI | FP | DB | BA | CR | GF | YF | GIF | JG | PR | CO | CN | SY |
|---|---|---|---|---|---|---|---|---|---|---|---|---|---|---|---|---|
| 2,6-(CH$_3$)$_2$-C$_6$H$_3$-N(CH(CH$_3$)$_2$)-CO-CH$_2$Cl | 1.12 | 0 | 3 | 8 | 9 | 9 | 9 | 9 | 8 | 8 | 9 | 8 | 9 | 0 | 0 | 0 |
|  | 0.56 | 0 | 0 | 7 | 8 | 8 | 9 | 9 | 8 | 9 | 7 | 6 | 7 | 0 | 0 | 0 |
|  | 0.28 | 0 | 0 | 6 | 8 | 6 | 9 | 9 | 7 | 6 | 7 | 8 | 7 | 0 | 0 | 0 |
|  | 0.14 | 0 | 0 | 0 | 6 | 3 | 6 | 7 | 7 | 3 | 5 | 3 | 5 | 0 | 0 | 0 |
|  | 0.07 | 0 | 0 | 0 | 6 | 3 | 5 | 7 | 6 | 2 | 3 | 0 | 0 | 0 | 0 | 0 |
|  | 0.035 | 0 | 0 | 0 | 0 | 0 | 3 | 6 | 5 | 0 | 2 | 0 | 0 | 0 | 0 | 0 |
| Compound of the Invention 2-CH$_3$,4-CH$_3$,6-CH$_3$-C$_6$H$_2$-N(CH(CH$_3$)$_2$)-CO-CH$_2$Cl | 1.12 | 0 | 0 | 3 | 9 | 3 | 8 | 8 | 8 | 9 | 9 | 8 | 7 | 0 | 0 | 0 |
|  | 0.56 | 0 | 0 | 0 | 9 | 3 | 9 | 9 | 7 | 7 | 7 | 8 | 7 | 0 | 0 | 0 |
|  | 0.28 | 0 | 0 | 0 | 7 | 0 | 7 | 7 | 7 | 5 | 3 | 5 | 3 | 0 | 0 | 0 |
|  | 0.14 | 0 | 0 | 0 | 7 | 0 | 8 | 7 | 7 | 2 | 5 | 3 | 2 | 0 | 0 | 0 |
|  | 0.07 | 0 | 0 | 0 | 6 | 0 | 6 | 7 | 6 | 0 | 3 | 0 | 0 | 0 | 0 | 0 |
|  | 0.035 | 0 | 0 | 0 | 3 | 0 | 0 | 5 | 2 | 0 | 0 | 0 | 0 | 0 | 0 | 0 |

Compound of the Invention

We claim:
1. The compound, 2-chloro-N-isopropyl-3',5'-dimethylacetanilide.
2. The compound, 2-chloro-N-isopropyl-3',4',5'-trimethylacetanilide.

* * * * *